United States Patent
Zhou et al.

(10) Patent No.: US 6,576,214 B2
(45) Date of Patent: Jun. 10, 2003

(54) CATALYTIC DIRECT PRODUCTION OF HYDROGEN PEROXIDE FROM HYDROGEN AND OXYGEN FEEDS

(75) Inventors: Bing Zhou, Cranbury, NJ (US); Michael A. Rueter, Plymouth Meeting, PA (US); Lap-Keung Lee, West Windsor, NJ (US); Bruce P. Pelrine, Ewing, NJ (US)

(73) Assignee: Hydrocarbon Technologies, Inc., Lawrenceville, NJ (US)

( * ) Notice: Subject to any disclaimer, the term of this patent is extended or adjusted under 35 U.S.C. 154(b) by 0 days.

(21) Appl. No.: 09/867,190

(22) Filed: May 29, 2001

(65) Prior Publication Data

US 2002/0106320 A1 Aug. 8, 2002

Related U.S. Application Data

(63) Continuation-in-part of application No. 09/733,154, filed on Dec. 8, 2000, now Pat. No. 6,500,968.

(51) Int. Cl.[7] ............... C01B 15/01; C07D 301/12; C07D 301/06
(52) U.S. Cl. ............... 423/584; 549/518; 549/523; 549/531
(58) Field of Search ............... 423/584; 549/531, 549/518, 523

(56) References Cited

U.S. PATENT DOCUMENTS

| | | | |
|---|---|---|---|
| 4,007,256 A | 2/1977 | Kim et al. | 423/584 |
| 4,128,627 A | 12/1978 | Dyer et al. | 423/584 |
| 4,335,092 A | 6/1982 | Dalton et al. | 423/584 |
| 4,336,239 A | 6/1982 | Dalton et al. | 423/584 |
| 4,336,240 A | 6/1982 | Moselay et al. | 423/584 |
| 4,347,231 A | 8/1982 | Michaelson | 423/584 |
| 4,347,232 A | 8/1982 | Michaelson | 423/584 |
| 5,104,635 A * | 4/1992 | Kanada et al | 423/584 |
| 5,338,531 A * | 8/1994 | Chuang et al. | 423/584 |
| 5,399,344 A | 3/1995 | Kawakami et al. | 423/584 |
| 5,961,948 A * | 10/1999 | Wanngard | 423/584 |
| 5,965,101 A * | 10/1999 | Goto et al. | 423/584 |
| 6,168,775 B1 * | 1/2001 | Zhou et al. | 423/584 |
| 6,284,213 B1 * | 9/2001 | Paparatto et al. | 423/584 |

* cited by examiner

*Primary Examiner*—Wayne A. Langel
(74) *Attorney, Agent, or Firm*—Daniel M. Kennedy; Fred Wilson

(57) ABSTRACT

A process for catalytically directly producing hydrogen peroxide ($H_2O_2$) product from hydrogen and oxygen-containing feeds by contacting them with a supported noble metal phase-controlled catalyst and a suitable organic liquid solvent having a Solvent Selection Parameter (SSP) between $0.14 \times 10^{-4}$ and $5.0 \times 10^{-4}$ at reaction condition of 0–100° C. temperature and 100–3,000 psig pressure. Unconverted feed gas and organic liquid solvent solution are usually recovered and recycled back to the reactor along with any recovered catalyst. If desired, the hydrogen peroxide product can be fed together with an organic chemical feedstock such as propylene and with the organic liquid solvent solution into a second catalytic reaction step which oxidizes the feedstock to produce a desired crude oxidized organic product such as propylene oxide, which may be purified by distillation steps and recovered from the solvent solution.

23 Claims, 4 Drawing Sheets

CORRELATION OF HYDROGEN PEROXIDE YIELD TO SOLVENT SELECTION PARAMETER

CATALYTIC DIRECT PRODUCTION OF HYDROGEN PEROXIDE FROM HYDROGEN AND OXYGEN FEEDS

This is a continuation-in-part application of Ser. No. 09/733,154, filed Dec. 8, 2000 U.S. Pat. No. 6,500,968.

BACKGROUND OF THE INVENTION

This invention pertains to production of hydrogen peroxide by catalytic direct synthesis from hydrogen and oxygen-containing feedstreams. It pertains particularly to a process for directly producing hydrogen peroxide ($H_2O_2$) product utilizing an active supported noble metal phase-controlled catalyst in a liquid medium containing an organic solvent and water for providing high activity and product selectivity to the process, and can utilize feedstreams containing low safe hydrogen concentrations below their lower flammability limit.

Demand for hydrogen peroxide product has been growing globally at about 6% annually, and in North America at about 10% annually. Such demand growth is due primarily to the enviromnental advantages of hydrogen peroxide usage, which upon decomposition releases only oxygen and water. Hydrogen peroxide is an effective replacement for chlorine in pulp and paper bleaching, water treatment and other environmental processes, and meets the growing product demand and need for a simple environmentally friendly and cost effective process that can be located on-site for the pulp, paper and other manufacturing facilities. The hydrogen peroxide presently being produced commercially uses a known anthraquinone process which has low yields and some safety problems. Also, transportation of hydrogen peroxide from a production site to an end-user facility is an important safety issue due to the risk of explosion of hydrogen peroxide by its violent decomposition.

Many attempts have been made to produce hydrogen peroxide directly from hydrogen and oxygen-containing feedstreams, because such a process not only has potential for significantly reducing production cost, but also provides an alternative production process which avoids the present use of toxic feedstock and working solutions. For such direct catalytic production of hydrogen peroxide, the feedstreams are hydrogen and air which are clean and environmentally harmless. Such direct catalytic process generates no waste and is cost efficient due to its inherent simplicity, and the hydrogen peroxide product can be used directly as a bleaching agent in pulp and paper processes. However, such proposed direct production technology has not yet been commercialized, as the major problems for the known such processes are (1) hazardous operating conditions (with the feed hydrogen partial pressure within the flammable or explosive range), (2) low reaction rates, and (3) low catalytic product selectivity.

Although the direct catalytic synthesis of hydrogen peroxide product has attracted much attention and many patents have been issued, none of the patented processes have been commercially feasible due to low catalyst activity and low selectivity for the hydrogen peroxide product. Until the early 1990's most of these patents utilized as feed gas at least 10% hydrogen in air or oxygen, which is within the flammabiltiy limits for the $H_2/O_2$ mixture. Due to increasing safety concerns, the recent approach has been to utilize feedstreams having hydrogen concentration below about 5 vol. %. However, at such low hydrogen concentration, the catalysts used must be much more active to achieve an acceptable production rate for hydrogen peroxide. Highly dispersed palladium on various support materials has been used to enhance the catalytic activity. However, the dispersion methods used have not adequately controlled the crystal phase of the palladium, and the desired improvement in selectivity towards hydrogen peroxide product has not been achieved. A main problem in preparing a highly selective catalyst for hydrogen peroxide production is how to consistently control the formation of desired metal phase such as phase 110 or 220, etc. in the catalyst.

Most of the known prior processes for direct hydrogen peroxide catalytic synthesis are based on use of an aqueous liquid medium for conducting the synthesis reaction, as hydrogen peroxide is generally produced commercially as an aqueous product. Use of organic compounds in combination with hydrogen peroxide can raise safety concerns related to the unintended formation of organic peroxides which can be fire or explosion hazards, especially if accidentally concentrated for example by precipitation. However, there are some prior art patents disclosing direct synthesis of hydrogen peroxide in liquid mediums that include an organic solvent. One class of such prior art processes involves the use of a liquid medium consisting of a two-phase mixture of water and an organic solvent which is immiscible with water. In general, the operating principle of such prior art processes is that the peroxide synthesis catalyst is contained in the organic phase, such that hydrogen peroxide synthesis occurs in this phase. But the resulting hydrogen peroxide product is poorly soluble in that phase, so the peroxide is extracted into the aqueous phase, segregating the product from the catalyst and preventing undesired product degradation.

U.S Pat. No. 4,128,627 discloses hydrogen peroxide being synthesized in a two-phase mixture using a homogeneous palladium-based catalyst which is insoluble in water, with preferred organic solvents being 1,2-dichlorobenzene, chlorobenzene and xylene. A critical function of the organic solvent component is to dissolve the homogeneous catalyst, which is insoluble in the aqueous phase. The best results reported are a hydrogen peroxide product concentration of only 0.45 wt % and a product yield of only 11.59 g $H_2O_2$/g Pd/hr, but requiring an undesirably high hydrogen feed concentration of 97.2 vol. %. In U.S. Pat. No. 4,336,240, it is disclosed that when the organic solvent is a fluorocarbon or halofluorocarbon such as 1,1,2-trichloro-trifluoroethane, a somewhat higher hydrogen peroxide product concentration of 3.2 wt % is achieved, but at a reduced yield of only 0.99 g $H_2O_2$/g Pd/hr, and again with very high hydrogen concentration in the feed gas.

U.S. Pat. Nos. 4,347,231 and 4,347,232 utilize the same two-phase liquid medium concept using homogeneous iridium-based and palladium-based catalysts, respectively, and preferred organic solvents are toluene, xylene, and chlorinated solvents such as dichloromethane. Again, the key operating principle is that the organic solvent is present to dissolve the water-insoluble homogeneous catalyst, and the water phase is present to extract the peroxide product away from the organic phase. The best results were 1.7% $H_2O_2$ product concentration and 89 g $H_2O_2$/g Pd/hr yield, but with undesired high hydrogen feed concentrations of 50 vol. % which are well above the explosion limit.

For U.S. Pat. No. 5,399,334 a two-phase liquid reaction medium is used, wherein the organic solvent is a halogenated organic, especially hydrocarbons substituted by at least three fluorine atoms. The best results reported were only 0.8 wt. % $H_2O_2$ product concentration at a yield of 266 g $H_2O_2$ g Pd/hr, or 3.5 wt % $H_2O_2$ product concentration at a yield 194 g $H_2O_2$/g Pd/hr.

Another group of prior art processes in which organic solvents are used as at least part of the liquid medium for direct catalytic hydrogen peroxide synthesis is those patents where only a single liquid phase is present. For example, U.S. Pat. No. 3,361,533 utilizes a liquid mixture of water with a soluble organic solvent such as alcohol or ketone, with acetone being mentioned as the best organic solvent, and the catalyst is a heterogeneous supported noble metal, especially palladium (Pd). A high hydrogen feed concentration of 16.7 vol. % is used, which is well above the flammability limit and close to the explosion limit, but the hydrogen peroxide yield was only 4.86 g $H_2O_2$ g Pd/hr.

U.S. Pat. No. 4,007,256 utilizes a one-phase liquid reaction medium consisting of water mixed with an organic nitrogen-containing compound such as acetonitrile, and a supported palladium catalyst. A high hydrogen feed concentration of 50 vol. % was used, again well above the explosive limit, and the best hydrogen peroxide product concentration was 6.4 wt %, with a product yield of 160 g $H_2O_2$/g Pd/hr.

U.S. Pat. No. 4.335,092 uses a liquid reaction medium of primarily methanol with a small amount of formaldehyde, with the catalyst being supported palladium. Although the gas-phase hydrogen feed concentration was a safe level of 4.2 vol. %, the product hydrogen peroxide concentration was only 1.7 wt %, with a yield of only 12.1 g $H_2O_2$/g Pd/hr.

U.S. Pat. No. 4,336,239 utilizes a reaction liquid comprising a mixture of water and an organic solvent containing oxygen or nitrogen. Acetone is the preferred solvent, and the catalyst is a supported noble metal such as palladium. An undesirably high hydrogen gas-phase feed concentration of 22.6 vol. % was used, and the best hydrogen peroxide product concentration reported was 3.4 wt %, at a yield of 94 g $H_2O_2$/g Pd/hr.

It is apparent that while the prior art discloses use of liquid reaction medium for catalytic hydrogen peroxide synthesis including at least in part an organic solvent, the performance results of these prior processes for hydrogen peroxide product concentration and product yield are not notably better than most results reported for the direct catalytic synthesis of hydrogen peroxide in a purely aqueous liquid medium. Moreover, the most promising results were generally obtained using dangerously high hydrogen gas-phase feed concentrations.

SUMMARY OF THE INVENTION

The present invention provides a significantly improved process for catalytic direct synthesis of hydrogen peroxide ($H_2O_2$) product from hydrogen and oxygen-containing feeds, utilizing an active supported noble-metal phase-controlled catalyst in combination with a liquid medium containing at least some organic solvent, which combination of catalyst and liquid solvent provides unexpectedly large improvements in hydrogen peroxide concentration and yield as compared to utilizing a purely aqueous liquid medium. The particulate noble metal catalyst useful in this invention is insoluble in the liquid medium. The preferred supported noble metal phase-controlled catalyst of this invention includes a particulate support material having total surface area of 50–500 m$^2$/gm; and 0.01–10 wt. % noble metal controllably deposited on the particulate support material, the noble metal having a wide distribution of minute crystals each having size of 0.5–100 nanometers (nm), and atoms of the noble metal being exposed in an orderly linear alignment pattern on the support material, so that at least most of the noble metal crystals have a phase exposition of 110 and/or 220, with the noble metal being palladium, which can be used in combination with platinum, gold, iridium, osmium, rhodium, or ruthenium, and combinations thereof. This preferred catalyst is disclosed in our U.S. Pat. No. 6,168,775, which is being incorporated herein by reference to the extent necessary to adequately disclose the present invention. For this preferred catalyst, the noble metal constituent is present as nano-size particles having a controlled phase exposition, thereby assuring that only the most active and selective noble metal catalytic sites are available for reaction with the liquid solvent medium.

A critical feature of this invention is the unexpected discovery of a significant performance enhancement achieved by conducting the catalytic direct synthesis reaction in a liquid medium including, at least in part, a selected organic solvent. This solvent solution discovery is contrary to the teachings of the prior art, from which no significant improvement in product concentration or yield would be suggested by using a organic solvent reaction medium for catalytic direct hydrogen peroxide synthesis of hydrogen peroxide product. Although a variety of known organic solvents may be used in this invention, the appropriate solvent selection is influenced by various factors, including catalyst performance enhancement, ease of separating the liquid solvent from the peroxide-containing liquid product for recycle, ultimate use for the hydrogen peroxide product, and the possibility of side reactions occurring between the solvent and the hydrogen peroxide which might form undesirable non-selective products or pose a safety hazard. The organic solvent may be used as a pure solvent, or as a mixture with water, with the selection related to similar factors as defined by a unique Solvent Selection Parameter (SSP). The Solvent Selection Parameter is defined based on the solubility of hydrogen in the solvent, and is specifically defined as follows:

$$\text{Solvent Selection Parameter} = \Sigma(w_i \times S_i)$$

where:
- $w_i$ is the weight fraction of solvent component i in the liquid reaction mixture,
- $S_i$ is the solubility of hydrogen in pure component i, expressed as mole fraction at standard conditions of 25° C. and 1 atm, and
- the symbol $\Sigma$ indicates a sum over all of the components that comprise the liquid reaction mixture.

This Solvent Selection Parameter (SSP) is simple to calculate based on hydrogen solubility data that are available in the open literature. Although this Solvent Selection Parameter takes no account of non-linear changes in hydrogen solubility that may occur upon mixing different liquids, it has been found to be very useful in selection of appropriate organic solvents for the liquid medium for the practice of this invention This Solvent Selection Parameter of this invention has been found to correlate strongly to a key measure of process performance, namely the catalyst hydrogen peroxide yield, which is defined as the weight of hydrogen peroxide produced per weight of active noble metal per hour. For a series of liquid reaction mixtures comprising water, pure organic solvent, or mixtures of water and solvent, the Solvent Selection Parameter was calculated, and the catalyst hydrogen peroxide yields were measured in laboratory catalyst performance tests. These data results are shown numerically in Table 1, and are also shown graphically in FIG. 1.

As evident in FIG. 1, there is a strong linear correlation between the Solvent Selection Parameter (SSP) and the catalyst hydrogen peroxide yield, with improved yield being achieved as the Solvent Selection Parameter is increased. The comparative benchmark is the use of water alone as the liquid reaction medium, which has a Solvent Selection Parameter of $0-14\times10^{-4}$, and gives a catalyst hydrogen peroxide yield of 207 g $H_2O_2$/g Pd/hr in performance test. By using different solvents or solvent/water mixtures that have higher Solvent Selection Parameters, higher yields up to about 900 g $H_2O_2$/g Pd/hr can be achieved. These results demonstrate that increased hydrogen solubility in the solvent medium is a controlling factor that improves the hydrogen peroxide concentration and yield. For the purposes of this invention, the liquid reaction medium will have a Solvent Selection Parameter that is greater than $0.14\times10^{-4}$, and not exceeding about $5.0\times10^{-4}$. Preferred liquid solvents will have a Solvent Selection Parameter between $0.2\times10^{-4}$ and $4.0\times10^{-4}$.

While FIG. 1 shows a generally linear increase in catalyst hydrogen peroxide yield with increases in the Solvent Selection Parameter (SSP), such an increase is not sustained indefinitely. An upper limitation has been discovered for appropriate values of the Solvent Selection Parameter for the practice of this invention. This limitation derives from the fact that the preferred solvents should be soluble in water, and that the liquid reaction mixture should comprise a single liquid phase. Organic solvents with the highest hydrogen solubility are generally those which are highly hydrophobic, including widely used solvents like paraffinic hydrocarbons such as hexane and the like, and aromatic hydrocarbons such as benzene, toluene, and the like. While liquid reaction mixtures comprising all or part of solvents of this type have relatively high Solvent Selection Parameter values, they are not preferred for the practice of this invention because they have poor miscibility with water. Hydrogen peroxide is not sufficiently soluble in these solvents, thereby hindering the critical step of product desorption from the catalyst surface into the surrounding liquid medium. This desorption problem causes the hydrogen peroxide product to remain at or near the catalyst surface, where it tends to undergo further chemical reaction to form undesired water by-product, resulting in poor catalyst hydrogen peroxide yields. Therefore, for the practice of this invention, the liquid reaction medium should have a Solvent Selection Parameter (SSP) values less than $5.0\times10^{-4}$, and preferably less than $4.0\times10^{-4}$.

Useful organic solvents for this invention include oxygen-containing compounds such as alcohols, ketones, aldehydes, furans (e.g. THF), ethers, and esters, nitrogen-containing compounds such as nitrites, amines, and amides (e.g. DMF), phosphorus containing compounds such as organic phosphine oxides (e.g. Cyanex products produced by Cytec), hydrocarbons such as aliphatic hydrocarbons and aromatic hydrocarbons, and the like, or mixtures thereof. Preferred solvents are those which are miscible with water and have good solubility for hydrogen peroxide, because it has been found in the practice of this invention that a one-phase liquid reaction medium provides superior yield results. Furthermore, it is preferred that the solvent have a boiling point temperature lower than that of water or hydrogen peroxide, which allows the solvent to be recovered from the peroxide-containing product as an overhead stream by a distillation step. Such lower boiling temperature relationship avoids the need to distill hydrogen peroxide overhead from a heavier solvent, which is a hazardous operation. Examples of preferred solvents are light alcohols such as ethanol, methanol, n-propanol and isopropanol, light ketones such as acetone, and nitrogen-containing solvents such as acetonitrile and 1-propylamine.

In the process of this invention, the yield of hydrogen peroxide based on the catalyst may be improved by the addition of a suitable promoter to the reaction medium. Examples of effective promoters are halide salts such as sodium bromide, sodium chloride, sodium iodide, and the like. By adding a halide salt in an amount in the range of 1 ppm to 500 ppm by weight of the liquid reaction medium, and preferably 3 ppm to 200 ppm, the catalyst hydrogen peroxide yield can be substantially improved.

Referring to FIG. 1, it is evident that the addition of a promoter is only effective when the desired concentration of promoter is fully soluble in the liquid mixture. For the data points along the upper curve "A" of FIG. 1, 5 ppm by weight of sodium bromide (NaBr) was added to the liquid mixture. The solubility of NaBr in these liquid mixtures was greater than 5 ppm, so that the amount of added NaBr dissolved completely. In these cases, the catalyst hydrogen peroxide yield rises rapidly as the Solvent Selection Parameter (SSP) is increased, so that greater than a four-fold increase in yield is achieved relative to the comparative case of using only water as the liquid reaction solvent by increasing the Solvent Selection Parameter from 0.14 to 1.6.

In cases where promoters such as halide salts are either not used or are insoluble in the liquid solvent mixture, lesser results are achieved as shown by to the lower curve "B" of FIG. 1. In these cases, increases in SSP also result in improved catalyst hydrogen peroxide yield, but the rate of increase is lower than when the NaBr promotor is used. However, catalyst hydrogen peroxide yields achieved for higher values of SSP, even in the absence of a promoter, are substantially greater than those achieved at low values of SSP with a promoter. Relative to the comparative case of using water as the reaction medium with NaBr soluble promoter, catalyst hydrogen peroxide yields in the absence of promoter are increased almost four-fold by increasing the SSP value to $2.7\times10^{-4}$.

Therefore, in the practice of this invention utilizing the desired Solvent Selection Parameter (SSP) values, substantial improvements in catalyst hydrogen peroxide yields are advantageously achieved relative to the known prior art processes, either with or without use of promoters such as halide salts in the reaction medium. By using such preferred promoters in combination with liquid mixtures in which they are soluble, higher catalyst hydrogen peroxide yields are achieved. Such use of soluble promotors can advantageously result in smaller reactor size and reduced catalyst requirement, which lowers capital and operating costs for the process. However, depending on the ultimate use for the hydrogen peroxide product, the presence of such promoters in the product may not be acceptable, and would require separation of the promoter from the reaction product, which would add some cost and complexity to the process.

While the liquid reaction medium may comprise an essentially pure organic solvent without water, it is preferable to conduct the hydrogen peroxide synthesis in a reaction medium which contains a portion of water. In commercial practice, the solvent fed to the catalytic peroxide synthesis reactor will be recovered and recycled back to the reactor from a point downstream in the process, and it is preferable to avoid any need to purify this solvent to a high degree, but instead to allow a fraction of water to be recycled along with the solvent, which reduces costs for distillation or other separations. Also, hydrogen peroxide is typically produced and marketed as an aqueous solution. If the purpose of the hydrogen peroxide produced by this process is commercial sale, then upon removal and recycle of the organic solvent, the presence of water in the reaction mixture will lead to the formation of an aqueous hydrogen peroxide solution which is suitable for further processing and commercial use.

DETAILED DESCRIPTION OF INVENTION

This invention provides a significantly improved process for producing hydrogen peroxide product by catalytic direct synthesis from hydrogen and oxygen-containing feed gases. This process produces hydrogen peroxide more efficiently, at lower cost, and requires substantially fewer steps than by using existing commercial processes. The present process can provide hydrogen peroxide as an aqueous solution suitable for purification and sale in conventional hydrogen peroxide markets, or it can provide a solution of hydrogen peroxide in an organic solvent which is suitable for use in other chemical processes, such as selective oxidation processes. Key features of this invention are the use of a highly active supported phase-controlled noble metal catalyst and the use of a specific liquid reaction medium which contains, at least in part, an organic solvent as defined by a Solvent Selection Parameter (SSP) having a value between $0.14 \times 10^{-4}$ and $5.0 \times 10^{-4}$. With these features, the present invention allows the economical production of hydrogen peroxide ($H_2O_2$) product from hydrogen and oxygen-containing feed gases, even when the hydrogen concentration in the gas phase is maintained below about 5.0 vol. %.

According to this invention, the above-mentioned noble metal phase-controlled catalyst is utilized in a process for catalytic direct production of hydrogen peroxide from hydrogen and oxygen-containing feed gases. The FIGS. 2 and 3 flowsheets show two versions of this process. The specific configurations shown in these flowsheets are not meant to restrict the scope of the invention, as numerous possible flowsheet variations will be obvious to those skilled in the art and are included in the scope of this invention.

Figure 2:
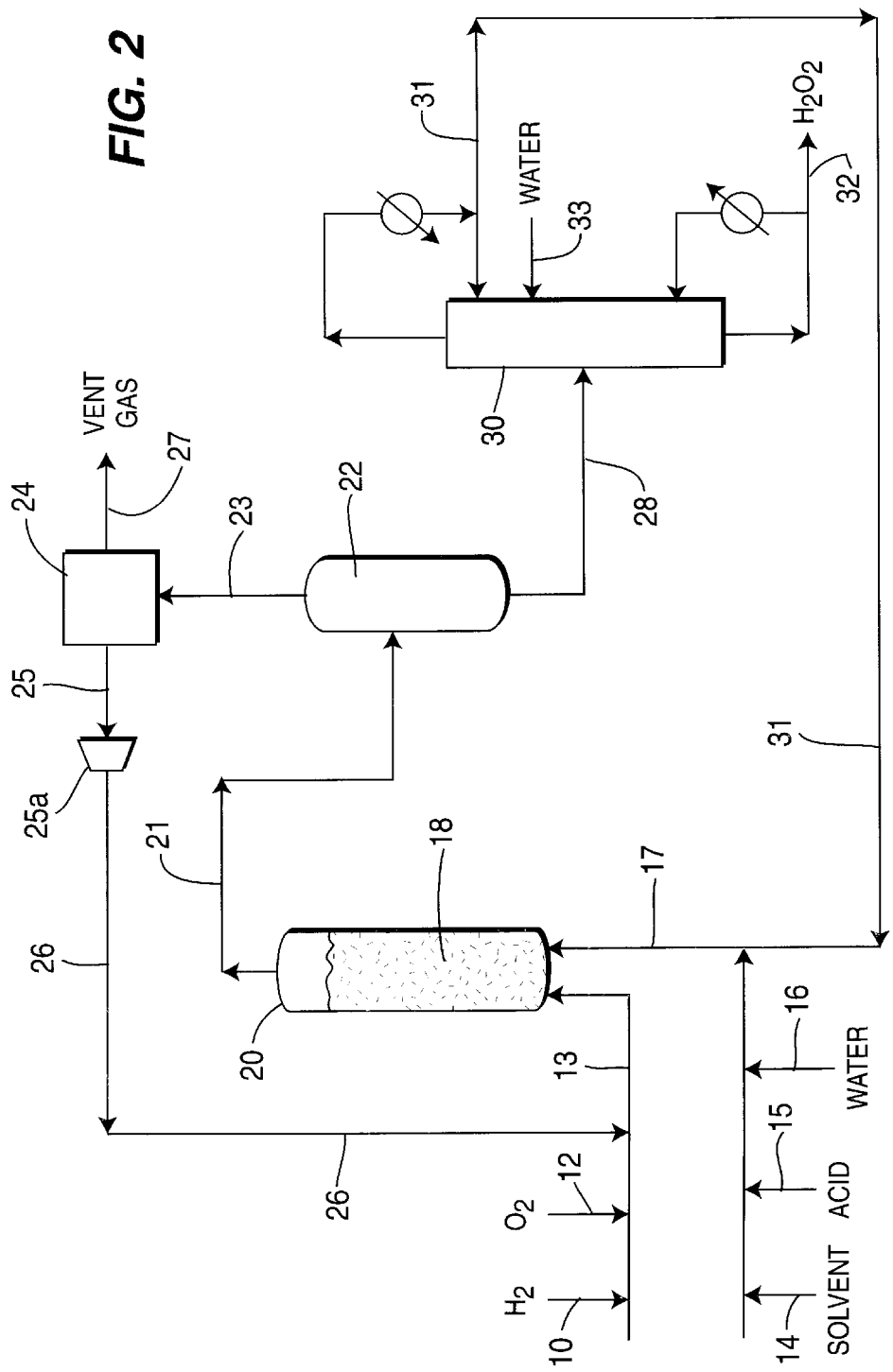
FIG. 2 shows a schematic flowsheet for a catalytic process of this invention for directly producing an aqueous hydrogen peroxide product from hydrogen and oxygen feeds, using a supported noble metal phase-controlled catalyst and a liquid reaction medium containing an organic solvent.

FIG. 2 shows an embodiment of the catalytic direct hydrogen peroxide production process in which the hydrogen peroxide product is produced as a aqueous solution suitable for further processing and purification. A hydrogen-containing feed gas is provided at 10, and may be purified hydrogen produced for example by the steam methane reforming process and purified by pressure swing absorption. Optionally, stream 10 could comprise other hydrogen-containing gases such as synthesis gas, refinery off-gas, or by-product gases from other processes. An oxygen-containing feed gas is provide at 12, and can comprise air, enriched air, or purified oxygen.

Optionally, a recycle gas stream recovered from a downstream location in the process may be provided at 26. The use for such a recycle gas stream 26 will be determined by various factors. If the single-pass hydrogen or oxygen percentage conversion in the peroxide synthesis reactor 20 is maintained at a relatively low value, for example less than about 80%, it will generally be necessary to recover and recycle a portion of the unreacted gases, because the loss of valuable reactant gases would otherwise be economically unacceptable. Also, if the feed gases 10 and 12 are costly purified gases, then it will generally be economically necessary to recover and recycle unreacted gases at 26 to avoid the loss of valuable feed components. However, if lower value feed gases such as air and/or low cost hydrogen are provided, or if the reactor conversion is maintained at a high level, then it could be preferable to omit the recycling of unreacted gases at 26, which would eliminate some costly process equipment such as a recycle compressor.

As shown in FIG. 2, these reaction feed gases 10, 12, and 26 are mixed together to form a combined gas feed stream at 13. For safety reasons, it is preferred that the gas phase composition of hydrogen in stream 13 be maintained below its lower flammability limit, which is 4–4.5 vol. % hydrogen depending on the composition of the gas stream 12. Although higher hydrogen concentrations can be used, this raises safety concerns which must be addressed by special design equipment.

Although FIG. 2 shows the feed gas streams being combined into a single stream 13 before being fed to the catalytic reactor 20, it will be understood that other flow configurations are possible. For example, the fresh hydrogen gas feed 10 may be injected directly into the reactor 20, which avoids mixing the fresh hydrogen into the oxygen-containing gases until after they are dispersed in the liquid reaction medium at 17. This arrangement could reduce the flammability or explosive hazard associated with mixing hydrogen and oxygen-containing gases, because gas bubbles dispersed in a liquid medium have a reduced chance of propagating a flame.

A fresh organic solvent liquid feed is provided at 14, and may comprise a variety of organic solvents or mixtures thereof as described above. Preferred solvents include, but are not limited to ethanol methanol, isopropanol, acetone, and acetonitrile. An acid feed is provided at 15, which may comprise a variety of acids including organic acids or inorganic acids. The acid at 15 is preferably an inorganic mineral acid such as sulfuric acid, phosphoric acid, or the like. The acid is added at 15 to adjust the pH of the liquid reaction medium in the reactor 20 into a preferred range of 0–5 for the best function of the supported noble metal phase-controlled catalyst 18 provided in the reactor 20.

Optionally, water may be provided at 16. The catalytic reaction for this invention can be conducted either in an essentially pure organic liquid solvent medium without water, or it may be conducted in a mixture of solvent and water. The solvent at 14 will preferably constitute at least 10% by weight of the liquid reaction medium, and more preferably at least 20% by weight. Even if water is not provided at 16, some water will be formed in the process as a non-selective by-product of the catalytic reaction of the hydrogen and oxygen feeds. Alternately, water can also be introduced at a point downstream in the process, as discussed below.

Recycled organic solvent recovered downstream in the process is provided at 31, and may constitute essentially pure solvent, but will preferably contain some water. While this water does not necessarily enhance the performance of the catalytic reaction in reactor 20, allowing an impure recycle solvent reduces costs for distillation or other downstream separations. The optimal concentration of water in the recycled solvent stream 31 will depend on several factors, including the choice of solvent, the cost of distillation or other separations, and the effect on catalyst activity and performance. As an example, if the selected organic solvent is one that forms a minimum boiling azeotrope with water, such as isopropanol, then it will be preferable for the recycle solvent at 31 to have a composition close to the azeotropic composition. Such composition avoids the need for any complicated or expensive separation steps as would be needed to overcome the azeotrope and produced purified solvent.

The combined gas feeds at 13 and liquid feeds at 17 are introduced into the catalytic reactor 20 containing a suitable catalyst 18 for hydrogen peroxide synthesis reaction. This reactor 20 may be provided in various forms, for example it may be a fixed bed type reactor operated in either upflow (bubble column) or downflow (trickle bed) mode, in which the particulate supported noble metal catalyst 18 is present as relatively large particles >1 mm. The reactor may be a continuous stirred tank reactor (CSTR), in which smaller size catalyst particles are suspended in the reaction liquid medium by action of a mechanical agitator means (not shown). Also, the reactor 20 may be a fluidized or ebullated catalyst bed type reactor, in which the catalyst particles 18 are suspended and agitated by the upflow of gases and liquids through the reactor. For this invention, it is preferred that the reactor 20 be a type in which the catalyst 18 is dispersed in the reaction liquid medium, such as a continuous stirred tank reactor (CSTR), an ebullated bed or fluidized bed type, or suspended bed, because these reactor configurations provide better interphase heat and mass transfer between gas, liquid, and catalyst particles than is provided by a catalytic fixed bed reactor type.

Depending on the physical size and form of the catalyst particles 18 and the type reactor 20 being used, the catalyst should preferably remain inside the reactor as shown in the FIG. 2 flowsheet. Alternatively, a portion of the catalyst may be carried out of the reactor by the exiting gas/liquid effluent stream 21. In the latter case, additional liquid/solid separation equipment is needed in the process to provide for the appropriate removal of catalyst particles from the reactor effluent stream, and recycle of recovered catalyst back to the reactor 20. Because of the high cost of the noble metal constituent in the noble metal catalyst 18, it is critical to effectively recover and reuse the catalyst. Such catalyst recovery can be accomplished by filtration, either internally within the reactor or externally in a separate unit operation, or by centrifugation, hydrocloning, gravity settling, or other suitable liquid/solids separation method.

Useful reaction conditions in the catalytic reactor 20 are 0–100° C. temperature and 100–3000 psig pressure. Preferred reaction conditions are 30–80° C. and 800–2500 psig. The proper catalyst concentration and liquid residence time in the reactor can be varied over a wide range, and will depend greatly on the type of reactor being utilized. For example, a stirred slurry reactor may typically use a solid catalyst loading of 10–30 vol % based on the total reactor volume. A suspended or ebullated bed reactor may typically use a solid catalyst loading of 20–40 vol. %, based on the volume of expanded catalyst bed. A fixed bed reactor will typically have a solid loading of 40–60 vol. % of the reactor volume. The correspondingly appropriate residence time for the liquid medium is based on the solid catalyst loading and the catalyst yield as provided elsewhere in this specification. As shown in FIG. 2, the reactor 20 is a single stage reactor, which is preferred as it minimizes equipment cost. However, it is also possible to conduct the catalytic reaction in two or more reaction stages connected together in either a parallel or a series flow arrangement.

From the reactor 20, the gas and liquid effluent stream 21 passes to a gas-liquid disengagement step 22. For clarity, this disengagement step 22 is shown as a single vessel located downstream from the reactor 20; however, some alternative arrangements are also possible. For example, the gas-liquid disengagement step 22 may be accomplished in a two-stage fashion, with an initial disengagement step being conducted at a pressure close to the reactor pressure, followed by depressurizing the liquid mixture to liberate dissolved gases and a second disengagement step for removing these gases. As another example, an initial high pressure gas-liquid disengagement step may occur within the reactor 20, in which case the reactor would be equipped with separate conduits for the exiting gas and liquid streams.

In the case that the reactor effluent stream 21 contains some suspended catalyst particles, a catalyst removal and recovery step would be included in the process, using one of the liquid/solid separation methods listed above. This could be accomplished before the gas-liquid disengagement step, but will preferably be conducted after at least the high pressure disengagement step to avoid the undesired complication of handling large volumes of gas passing through the catalyst separation equipment.

From the gas-liquid disengagement step 22 the overhead gas stream 23 is treated in unit 24, so that hydrogen and oxygen-containing gases at 25 are recompressed at recycle gas compressor 25a, which repressurizes the gas for recycle at 26 back to the reactor 20 inlet. The remaining gas may be vented to atmosphere at 27 by appropriate means to control buildup of feed gas impurities in the process, which may include impurities such as $CO_2$, $N_2$, or Ar. As discussed above, the necessity for this gas recycle stream 26 depends on several factors, including the single-pass reactant conversion in reactor 20 and the cost and purity of the feed gases at 10 and 12.

Also from the gas-liquid disengagement step 22, liquid product is withdrawn at 28 and passed to a solvent recovery step 30, in which the preferred solvent recovery method is distillation. Other recovery methods such as solvent extraction, membrane separation, or adsorption are also possible. It is preferred for the organic solvent to be light, i.e. have lower boiling point compared to water and hydrogen peroxide, so that the solvent can be distilled and removed overhead as stream 31 for recycle back to the reactor 20. While the distillation step 30 may be arranged to yield a purified solvent liquid at 31, it will be preferred economically to provide an impure solvent at 31 containing some fraction of water. Depending on the vapor-liquid equilibrium properties of the solvent-water system, the preferred water content of the overhead solvent stream 31 could be as high as 20–30 wt %, but will generally be less than 20 wt %.

From the distillation column 30, a bottoms liquid stream 32 is withdrawn as an aqueous hydrogen peroxide product. For safety considerations, it will generally be preferred to limit the concentration of hydrogen peroxide in stream 32 to a maximum of about 40 wt %. If the liquid stream 28 does not contain adequate water, it may be necessary to inject additional water at 33 directly into distillation column 30. Alternately, additional water may be mixed with the liquid feed stream 28 to the column 30.

The liquid product stream 32 contains hydrogen peroxide, water, and a small concentration of acid such as sulfuric acid. Depending on the intended use for the hydrogen peroxide product, this stream 32 may be useful as product, or may require additional purification. For example, if the hydrogen peroxide at 32 is being produced for commercial sale, it will generally be necessary to remove the acid, add peroxide stabilizers, and possibly distill the hydrogen peroxide up to a higher concentration of 50–70 wt. %. Such acid removal may be accomplished by ion exchange, membrane separation, adsorption, or other appropriate means (not shown). Appropriate hydrogen peroxide stabilizers are commercially available and known to those skilled in the art. Appropriate means for the distillation of hydrogen peroxide to produce concentrations of 50–70% or higher are known and commercially available.

Figure 3:
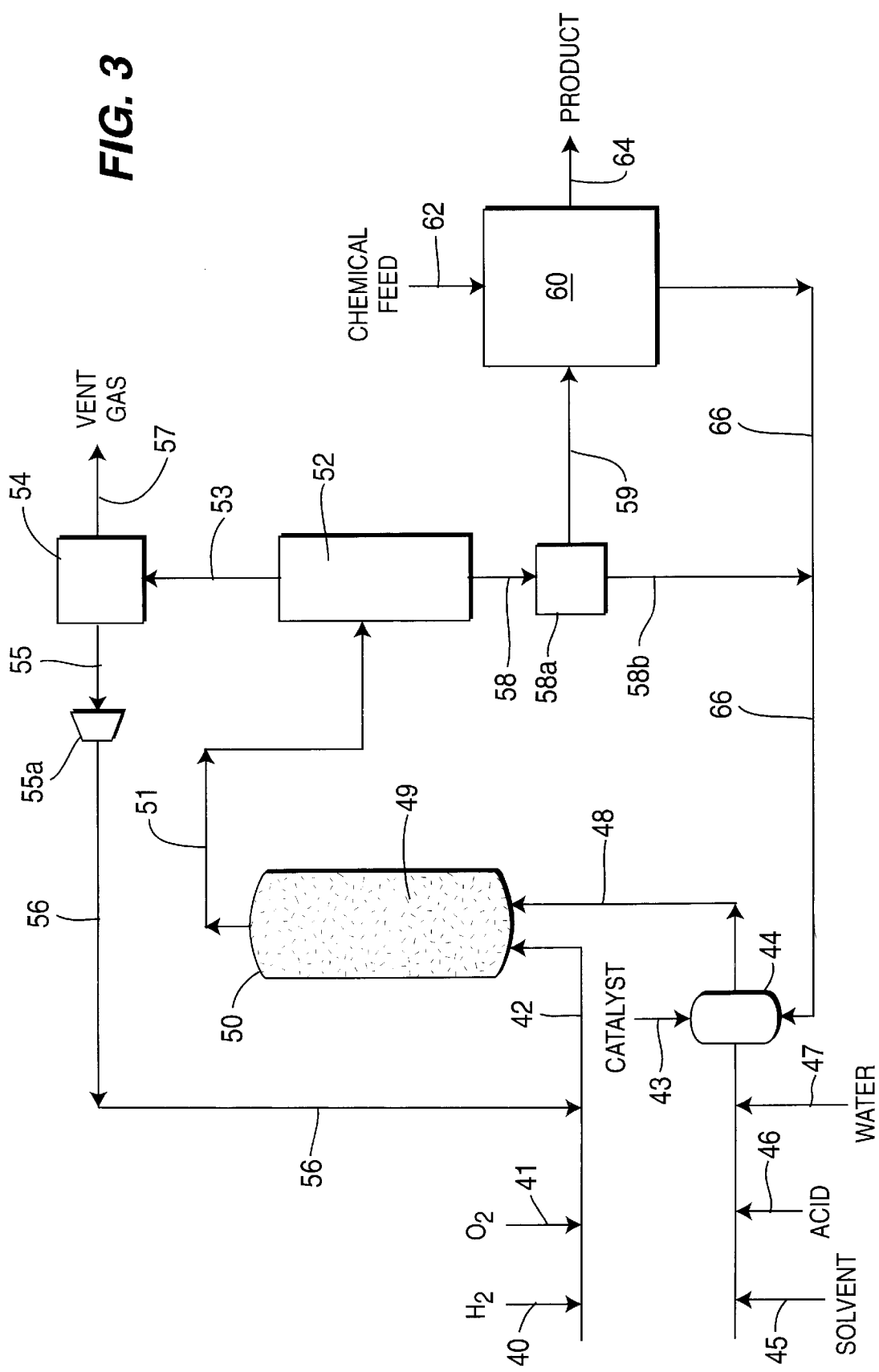
FIG. 3 shows an alternate embodiment for the catalytic direct production process in which a hydrogen peroxide intermediate product is produced in an organic solvent-containing medium, and then used directly in another oxidation process without removing the organic solvent.
Figure 4:
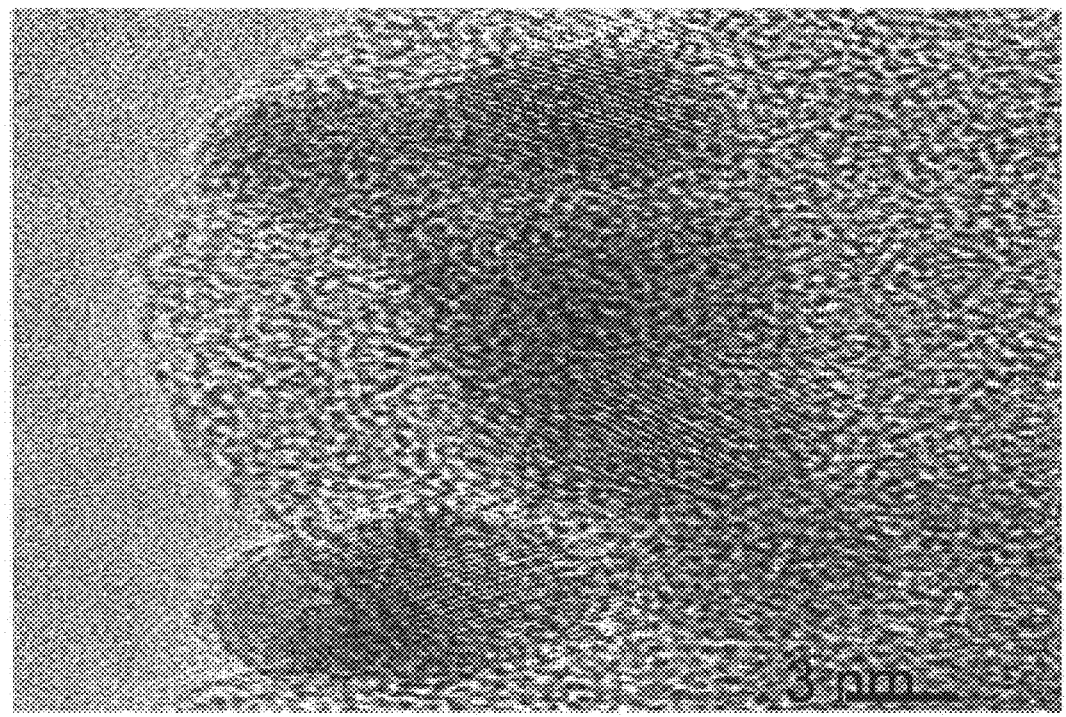

FIG. 3 shows an alternate embodiment for the process flowsheet of this invention, in which a hydrogen peroxide intermediate product is produced for direct use in another downstream oxidation process. For example, the hydrogen peroxide intermediate may be useful as an oxidizing agent in a selective oxidation reaction. As a specific but not limiting example, the hydrogen peroxide may be used for the epoxidation of propylene over a suitable catalyst to form propylene oxide product. It should be understood that the various process alternatives and options discussed above with respect to the FIG. 2 process generally apply equally to the FIG. 3 embodiment, with the exception of aspects of the distillation step at 30 which are omitted from the FIG. 3 process version.

In analogous fashion to the process of FIG. 2, feed gas streams are provided in the process of FIG. 3, including a hydrogen-containing gas 40, oxygen-containing gas 41, and a recycle gas 56 are combined as stream 42 and fed into catalytic reactor 50 containing catalyst bed 49. A particulate noble metal phase-controlled catalyst is provided at 43 to mixer vessel 44 together with an organic solvent 45, an acid 46, water 47, and recycle solvent at 66. These mixed streams at 48 are all fed into the catalytic reactor 50 containing particulate noble metal phase-controlled catalyst 49. The reactor 50 may be provided in several forms or types as discussed above for the FIG. 2 embodiment. But for this FIG. 3 embodiment, the catalyst 49 is in a liquid-slurry form. From reactor 50, the handling of the reactor effluent stream 51, the separation of gas and liquid at diengagement step 52, the handling of the disengaged gas 53 at treatment step 54 recycle gas 55 and vent gas 57 are all analogous to that for the process of FIG. 2. However, recovery and recycle of the supported noble metal catalyst 49 from the reactor 50 and included in liquid bottoms stream 58 is provided at a liquid-solids separation unit 58*a*, from which the catalyst is recycled at 58*b* back to the mixer vessel 44.

For the FIG. 3 embodiment, the handling of the liquid stream 59 from the gas-liquid disengagement step 52 differs in the process of FIG. 2. Instead of being distilled at column 30 to recover the organic solvent, the liquid stream 59 is fed directly to a downstream or subsequent oxidation process 60 which utilizes the hydrogen peroxide intermediate product. For the FIG. 3 process, such a subsequent oxidation process 60 is shown in simplified form, but it may in fact constitute a process consisting of many steps, including reactions, distillation, other separations, and the like. This process 60 utilizes the hydrogen peroxide contained in liquid stream 59 to produce a separate oxidized product at 64. Generally, the subsequent oxidation process 60 will utilize the hydrogen peroxide intermediate at 59 as an oxidizing agent to oxidize a chemical feed material provided at 62 to produce another desired product 64. This oxidation process 60 may be non-catalytic, or it may involve the use of a catalyst for a selective oxidation. Examples of appropriate feed materials at 62 may include, but are not limited to, olefins such as propylene, cyclohexene, or styrene, aromatics such as benzene, phenol, or toluene, ketones such as cyclohexanone, alkanes, or alcohols. Examples of appropriate products at 64 may include, but are not limited to, epoxides such as propylene oxide, cyclohexene oxide, or styrene oxide, hydroxylated aromatics such as phenol, hydroquinone, catechol, or p-cresol, oximes such as cyclohexanone oxime, aldehydes, acids, alcohols, or lactones.

In the subsequent oxidation process 60, the organic solvent liquid contained in stream 59 will be recovered and recycled as stream 66 back to the hydrogen peroxide catalytic synthesis reactor 50. Similarly as with the process of FIG. 2, it will be preferable in the process of FIG. 3 to allow this recycle solvent at 66 to contain a portion of water, thereby reducing the cost of recovering the solvent.

The practice of this invention will be described further by the following examples, which should not be construed as limiting the scope of the invention.

EXAMPLE NO. 1

Figure 1:
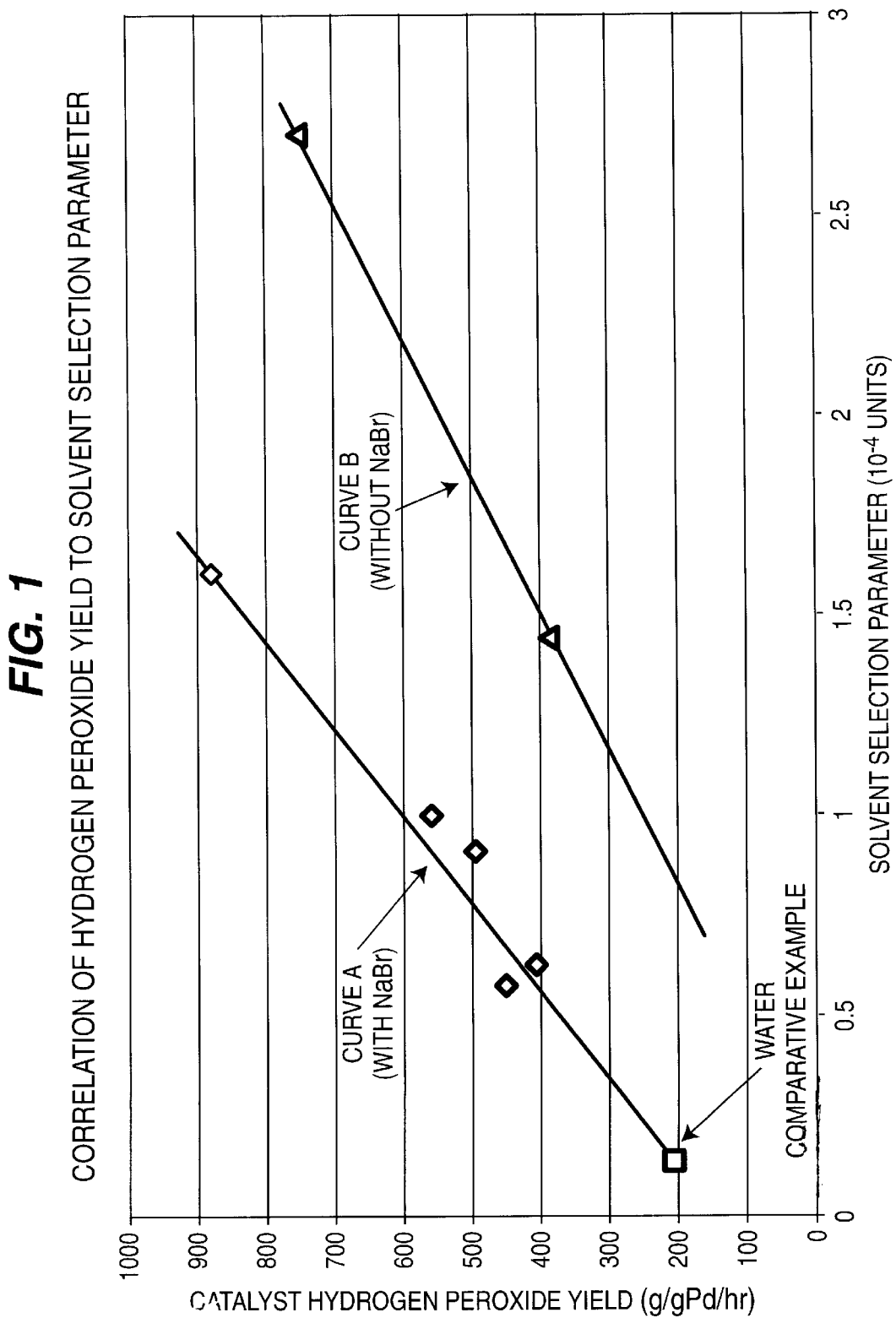
FIG. 1 is a graph showing the correlation of catalyst hydrogen peroxide product yield with a Solution Selection Parameter (SSP) defined according to this invention.

50 ml water and 0.5 g phase-controlled palladium catalyst were introduced into a 1-liter capacity stirred autoclave unit together with 1 wt. % sulfuric acid ($H_2SO_4$) and 5 ppm NaBr. and having a liquid Solvent Selection Parameter (SSP) of $0.14 \times 10^{-4}$. Reaction conditions were maintained at 45° C. temperature and 1400 psig pressure at gas feed rate of 1.0 liter/minute of feed gas containing 3% hydrogen in air. After 3 hours reaction time, hydrogen conversion reached to 24.3%. Liquid product was analyzed by titration with potassium permanganate, and 2.9 wt % concentration of hydrogen peroxide product was obtained at a yield of 207 g/g Pd/h. The examples and results are all tabulated in Table 1, and are shown graphically as FIG. 1.

EXAMPLE NO. 2

The water solvent in Example No. 1 was replaced by 75 ml of 30 vol. % methanol and 70 vol % water, having an increased Solvent Selection Parameter of $0.578 \times 10^{-4}$. The methanol was totally miscible with water, and 0.25 g phase-controlled palladium catalyst was used with 1 wt % $H_2SO_4$ and 5 ppm NaBr. After 2 hours reaction time, hydrogen conversion was 22.0% and 2.1 wt % concentration of hydrogen peroxide was obtained and yield increased to 450 g/g Pd/h.

EXAMPLE NO. 3

The methanol in Example No. 2 was replaced by acetonitrile which provided a Solvent Selection Parameter of $0.626 \times 10^{-4}$. The acetonitrile was miscible with water. After 2 hours reaction, hydrogen conversion was 18.9% and 1.9 wt % concentration of hydrogen peroxide was obtained with a yield of 407 g/g Pd/h.

EXAMPLE NO. 4

The methanol in Example No. 2 was replaced by 2-propanol, which increased the Solvent Selection Parameter to $0.908 \times 10^{-4}$. The 2-propanol was miscible with water. After 2 hours reaction, hydrogen conversion was 19.8% and 2.3 wt % concentration of hydrogen peroxide was obtained with a yield of 493 g/g Pd/h.

TABLE 1

Effect of Liquid Solvent on Hydrogen Peroxide Synthesis

| Example Number | Liquid Mixture | Catalyst to liquid ratio | $H_2$ Solubility in Solvent 1 atm 25 C. $10^{-4}$ mole fraction | $H_2$ Solubility in Water 1 atm 25 C. $10^{-4}$ mole fraction | Weight fraction solvent | Solvent Selection Parameter Weight Average $H_2$ Solubility $10^{-4}$ units | $H_2$ in Feed (vol. %) | $H_2$ Conversion (%) | $H_2O_2$ Concentration (wt %) | H2O2 Yield (g/gPd/h) |
|---|---|---|---|---|---|---|---|---|---|---|
| | | | | | Comparative Example | | | | | |
| 1 | Water | 1/100 | | 0.14 | 0 | 0.14 | 3 | 24.3 | 2.9 | 207 |
| | | | | Curve A Examples (with NaBr) | | | | | | |
| 2 | Methanol/Water | 1/300 | 1.6 | 0.14 | 0.3 | 0.578 | 3 | 22 | 2.1 | 450 |
| 3 | Acetonitrile/Water | 1/300 | 1.76 | 0.14 | 0.3 | 0.626 | 3 | 18.9 | 1.9 | 407 |
| 4 | Isopropanol/Water | 1/300 | 2.7 | 0.14 | 0.3 | 0.908 | 3 | 19.8 | 2.3 | 493 |
| 5 | Acetone/Water | 1/300 | 3 | 0.14 | 0.3 | 0.998 | 3 | 61.1 | 2.6 | 557 |
| 6 | Methanol | 1/300 | 1.6 | 0.14 | 1 | 1.6 | 3 | 85.2 | 4.1 | 879 |
| | | | | Curve B Examples (without NaBr) | | | | | | |
| 7 | DMF | 1/300 | 1.44 | 0.14 | 1 | 1.44 | 3 | 64.4 | 1.8 | 385 |
| 8 | Isopropanol | 1/300 | 2.7 | 0.14 | 1 | 2.7 | 3 | 82.4 | 3.5 | 750 |
| | | | | | Other Examples | | | | | |
| 9 | Hexane/Water * | 1/300 | 6.6 | 0.14 | 0.3 | 2.078 | 3 | 79 | 0 | 0 |
| 10 | Formaldehyde/Water | 1/300 | ? | 0.14 | 0.3 | ? | 3 | 11.8 | 0.3 | 64 |

* two-phase liquid mixture

EXAMPLE NO. 5

The methanol solvent in Example No. 2 was replaced by acetone which was totally miscible with water, and increased the Solvent Selection Parameter (SSP) to $0.998 \times 10^{-4}$. After 2 hours reaction, hydrogen conversion increased to 61.1% and 2.6 wt % concentration of hydrogen peroxide was obtained with yield increased to 557 g/g Pd/h.

EXAMPLE NO. 6

The methanol and water solvent in Example No. 2 was replaced with 75 ml pure methanol which has Solvent Selection Parameter (SSP) of $1.6 \times 10^{-4}$. After 2 hours reaction, hydrogen conversion increased to 85.2%. and 4.1 wt % concentration of hydrogen peroxide concentration was obtained at a yield of 879 g/g Pd/h.

EXAMPLE NO. 7

The methanol solvent in Example No. 6 was replaced by dimethyl form amide (DMF), which has a Solvent Selection Parameter (SSP) of $1.44 \times 10^{-4}$. The 5 ppm NaBr was not totally dissolved in the DMF. After 2 hours reaction, hydrogen conversion reached to 64.4% and 1.8 wt % concentration of hydrogen peroxide was obtained at a yield of 385 g/g Pd/h.

EXAMPLE NO. 8

The methanol in Example No. 6 was replaced by 2-propanol, providing a Solvent Selection Parameter (SSP) of $2.7 \times 10^{-4}$. The 5 ppm NaBr was not totally dissolved in the 2-propanol. After 2 hours reaction, hydrogen conversion increased to 82.4% and 3.5 wt % concentration of hydrogen peroxide was obtained at yield of 750 g/g Pd/h.

EXAMPLE NO. 9

The methanol in Example No. 6 was replaced by 30% hexane and 70% water, which increased the Solvent Selection Parameter (SSP) of $2.078 \times 10^{-4}$; 5 ppm NaBr was not dissolved in the hexane, but only in water. The hexane was not miscible with water. After 2 hours reaction, hydrogen conversion reached to 79.0%, but no hydrogen peroxide product was obtained.

EXAMPLE NO. 10

The hexane in Example No. 9 was replaced by formaldehyde, for which a Solvent Selection Parameter (SSP) value was not available from literature sources. The formaldehyde was totally miscible with water. After 2 hours reaction, hydrogen conversion was only 11.8%, and 0.3 wt % concentration of hydrogen peroxide product was obtained at yield of only 65 g/g Pd/h.

Although this invention has been disclosed broadly and includes preferred embodiments, it will be understood that modifications and variations can be made and that some features may be utilized without others all within the scope of the invention as defined by the following claims.

We claim:

1. A catalytic direct process for producing hydrogen peroxide ($H_2O_2$) product from hydrogen and oxygen-containing feedstreams, comprising the steps of:
   (a) providing a hydrogen-containing feed and oxygen-containing gaseous feed to a catalytic reactor;
   (b) providing a liquid mixture that includes at least some organic liquid solvent, said liquid mixture having a Solvent Selection Parameter (SSP) between $0.14 \times 10^{-4}$ and $5.0 \times 10^{-4}$;
   (c) providing a solid noble metal phase-controlled catalyst in said catalytic reactor;
   (d) contacting said hydrogen-containing and oxygen-containing feedstreams with said solid noble metal phase-controlled catalyst in the presence of said liquid mixture in said catalytic reactor at temperature of 0–100° C. and pressure of 100–3000 psig, for total residence time of 0.1 second to 5 hours, and forming an effluent stream containing gas and liquid fractions;
   (e) disengaging unreacted gases from the liquid fraction, which contains hydrogen peroxide; and (f) withdrawing a hydrogen peroxide-containing liquid product from the process.

2. The process of claim 1, wherein the Solvent Selection Parameter (SSP) of said liquid mixture is between $0.2\times10^{-4}$ and $4.0\times10^{-4}$.

3. The process of claim 1, wherein the hydrogen concentration in said hydrogen-containing feedstream is maintained below the flammability limit.

4. The process of claim 1, wherein said liquid mixture comprises a single liquid phase.

5. The process of claim 1, wherein said organic liquid solvent is soluble in water.

6. The process of claim 1, wherein said organic liquid solvent has a normal boiling point temperature lower than that of water.

7. The process of claim 1, wherein said organic liquid solvent is selected from methanol, ethanol, n-propanol, isopropanol, acetone, acetonitrile, 1-propyl amine, or mixtures thereof.

8. The process of claim 1, wherein said liquid mixture contains at least some water.

9. The process of claim 1, wherein said liquid mixture contains a halide salt promotor.

10. The process of claim 9, wherein said liquid mixture contains 1–500 ppm by weight sodium bromide (NaBr) promoter.

11. The process of claim 1, wherein said catalytic reactor contains said solid catalyst particles are dispersed and mobile within the reactor wherein the particles remain within the reactor, said reactor including ebullated bed, fluidized bed, and suspended bed type reactors.

12. The process of claim 1, wherein said catalytic reactor is selected from types wherein said solid catalyst particles are dispersed and mobile within the liquid mixture and substantially exit the reactor with the effluent liquid fraction stream, said reactor including fluidized bed, transport bed, and stirred tank slurry type reactors.

13. The process of claim 12, wherein a portion of said catalyst particles that exit said reactor along with the liquid fraction stream is recovered and recycled back to the reactor using a liquid/solid separation method step selected from filtration, centrifugation, hydrocloning, gravity settling, and combinations thereof.

14. The process of claim 1, wherein said catalytic reactor contains a fixed catalytic bed, in which said catalyst particles are substantially fixed and immobile in the reactor.

15. The process of claim 1, wherein the catalytic reaction conditions are maintained at temperature of 30–80° C., pressure of 500–2500 psig and total liquid residence time of 1 sec to 1 hour.

16. The process of claim 1, wherein said disengaged unreacted gas fraction is treated for recovering unreacted hydrogen and/or oxygen for recycle back to the catalytic reactor, and for rejecting inert and by-product gases using a separation method selected from membrane separation, absorption, adsorption, cryogenic distillation, and combinations thereof.

17. The process of claim 1, wherein said unreacted hydrogen and oxygen gases are recycled to said catalytic reactor.

18. The process of claim 1, wherein said liquid fraction is separated to recover said organic solvent for recycle back to the chemical reactor and produce a solvent-free hydrogen peroxide solution product.

19. The process of claim 18, wherein said separation method is distillation.

20. The process of claim 1, wherein said hydrogen peroxide-containing liquid product is passed directly to a downstream subsequent chemical oxidation process, wherein the hydrogen peroxide is used as a reactant for converting an organic chemical feedstock to a useful oxidized product from the subsequent chemical oxidation process.

21. The process of claim 20, wherein organic solvent is recovered from the subsequent chemical oxidation process and recycled back to the hydrogen peroxide synthesis reactor.

22. The process of claim 20, wherein said organic chemical feedstock is propylene and said oxidized product is propylene oxide.

23. A catalytic direct process for producing hydrogen peroxide ($H_2O_2$) product from hydrogen-containing and oxygen-containing feedstreams, comprising the steps of:

(a) providing hydrogen-containing and oxygen-containing gaseous feedstreams to an ebullated bed catalytic reactor;

(b) providing a liquid mixture that includes at least some organic liquid solvent, said liquid mixture having a Solvent Selection Parameter (SSP) between $0.2\times10^{-4}$ and $4.0\times10^{-4}$;

(c) providing a solid noble metal phase-controlled catalyst in said catalytic reactor;

(d) contacting said hydrogen-containing and oxygen-containing feedstreams with said solid noble metal phase-controlled catalyst as defined by claim 3 in the presence of said liquid mixture and a halide salt promotor material in said ebullated bed reactor at temperature of 0–100° C. and pressure of 100–3000 psig, for total liquid residence time of 0.1 second to 5 hours, and forming an effluent stream containing gas and liquid fractions;

(e) disengaging unreacted gases from said liquid fraction, and distilling the liquid fraction to produce a hydrogen peroxide product; and (f) recovering and recycling hydrogen-containing and oxygen-containing gases and liquid solvent back to said catalytic reactor.

* * * * *